United States Patent [19]
Tuba et al.

[11] 4,071,515
[45] Jan. 31, 1978

[54] TRIAMINO-ANDROSTANES AND A PROCESS FOR THE PREPARATION OF THE SAID COMPOUNDS

[75] Inventors: Zoltan Tuba; Maria Marsai; Katalin Biro; Laszlo Szporny; Egon Karpati; Szabolcs Szeberenyi, all of Budapest, Hungary

[73] Assignee: Richter Gedeon Vegyeszeti Gyar Rt., Budapest, Hungary

[21] Appl. No.: 709,323

[22] Filed: July 28, 1976

[30] Foreign Application Priority Data

Aug. 1, 1975 Hungary .................................. OE 574

[51] Int. Cl.² ............................................. C07J 17/00

[52] U.S. Cl. ......................... 260/239.5; 260/239.55 R; 260/397.5; 260/397.4

[58] Field of Search ...................................... 260/239.5

[56] References Cited

U.S. PATENT DOCUMENTS 3,872,091   3/1975   Hewett et al. .................... 260/239.5

OTHER PUBLICATIONS

Chem. Abstracts, vol. 53, (1959), Para. 5345(f).

*Primary Examiner*—Elbert L. Roberts
*Attorney, Agent, or Firm*—Karl F. Ross

[57] ABSTRACT

New triamino-androstanes with curare-type properties and a process for the preparation thereof are disclosed.

22 Claims, No Drawings

TRIAMINO-ANDROSTANES AND A PROCESS FOR THE PREPARATION OF THE SAID COMPOUNDS

The invention is directed to new triamino-androstanes, acid addition salts and quaternary salts thereof and to a process for the preparation of the same compounds.

The new triamino-androstane derivatives have the formula

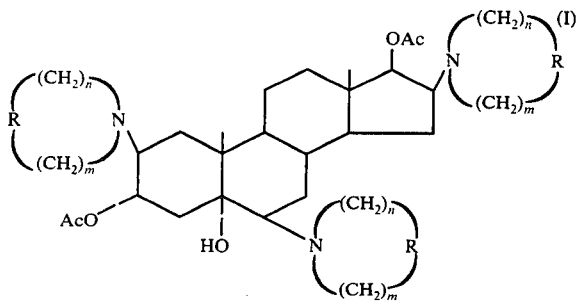

wherein
Ac represents an alkyl carbonyl group having 1 to 4 carbon atoms in the alkyl moiety,
R stands for a methylene group or an

group — wherein $R_2$ is a $C_{1-3}$ alkyl group and all the three substituents R are the same,
$n$ is 1 or 2
$m$ is 1, 2, 3 or 4. The di-quaternary salts thereof have the formula

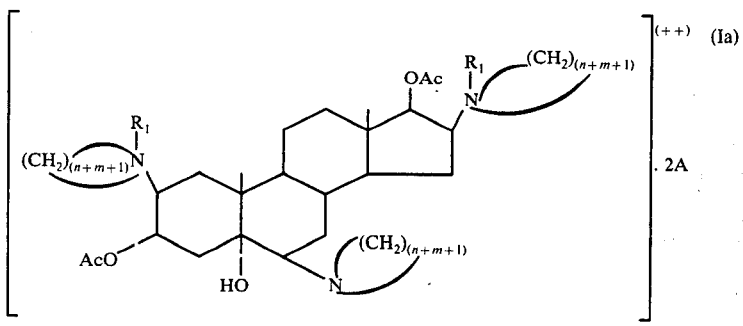

and the tri-quaternary salts thereof have the formula

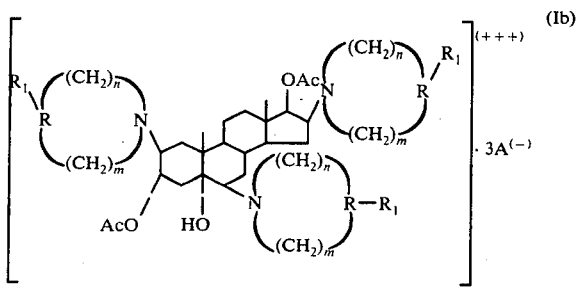

wherein

Ac, R, $n$ and $m$ are as defined above,
$R_1$ is $C_{1-5}$ alkyl or allyl and
A is a halogen atom.

According to the invention there are provided new compounds of the formula I, Ia and Ib, and new intermediate products: the compounds of the formulae I, II, III and IV. The preparation of the starting material of the synthesis is described in Example 1. The compounds of the formulae I, Ia and Ib are biologically active products and the intermediate products of the process also possess valuable biological activity. Compounds of the formulae Ia and Ib show curare type, non-depolarizing neuro-muscular blocking effect, i.e. they inhibit the implant of the nervous impuls on striated muscle, do not cause hystamine release, do not decrease blood pressure and their effect can be stopped by neostigmine. The compounds do not show any hormonal effect.

To determine the intensity and the duration of the activity cats subjected to anaesthesia and artificial respiration were tested.

The peroneus nerve was irritated electrically and the contraction of the tibialis muscle was registered, by intravenous administration of different doses of the blocking substances; the dose, inhibiting completely the muscle contraction ($ED_{100}$) was determined. The time between the starting effect and the restoration of the normal muscle reaction was measured. The data of the following table are related to the dose causing complete inhibition. As a referential substance pancuronium bromide (Negwer [1971] 4821) was used. (Advances in Steroid Biochemistry and Pharmacology [Briggs], W. R. Buckett: Aspects of the Pharmacology of Aminosteroids, 56-69, Br. J. Pharmac. Chemother. 32, 671-682 [1968], Arzneimittel-Forsch. 19, 1723-1726 [1969]).

| Compound | $ED_{100}$/mcg/kg/ | Duration of the effect/minutes |
|---|---|---|
| 2β,6β,16β-Tri-(4-dimethyl-piperazine)-3α,17β-diacetoxy-5α-hydroxy-androstane-tribromide | 6.8 | 180 |
| 2β,6β,16β-Tri-(4-propyl-4-methyl-piperazine)-3α,17β-diacetoxy-5α-hydroxy-androstane-tribromide | 7.1 | 220 |
| Pancuronium bromide | 18.0 | 23 |

The table shows, that the effective amount of the compounds is about 2.5 times smaller, than that of pancuronium bromide, and their effect lasts 9 to 10 times longer. Thus the compounds of the invention can be used in the first place in major surgery, since after a single dose a sufficient muscle relaxation can be achieved for the whole time of the operation.

The compounds of the invention of the formulae I, Ia, and Ib — wherein Ac, R, n, m, R₁ and A are defined above — can be prepared by reducing an epoxy-androstane-derivative, preferably 2α,3α;16α,17α-diepoxy-5α-hydroxy-6β-chloro-17β-bromo-androstane or 2α,3α; 16α,17α-diepoxy-5α,17β-diacetoxy-6β-chloro-androstane or 2α, 3α; 5α,6α;16α,17α-triepoxy-17β-bromo-androstane with a compound of the formula

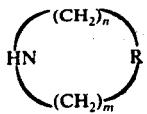

wherein R, n and m are as defined above — and reducing the obtained compound of the formula

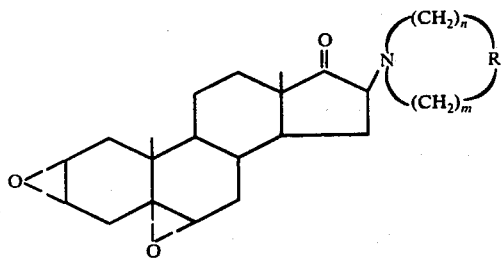

where the substituents are as defined above — and reacting the compound of the formula

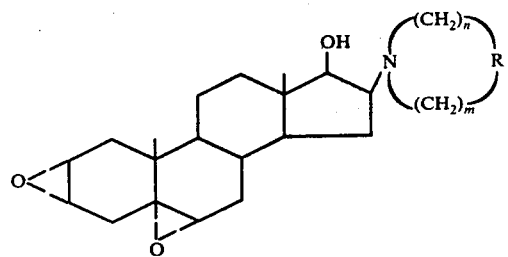

thus formed — where the substituents are as defined above — again with a compound of the formula V — wherein the substituents are as defined above — provided that when using the compound of the formula V repeatedly R is of the same meaning as in the first case and acylating the compound of the formula

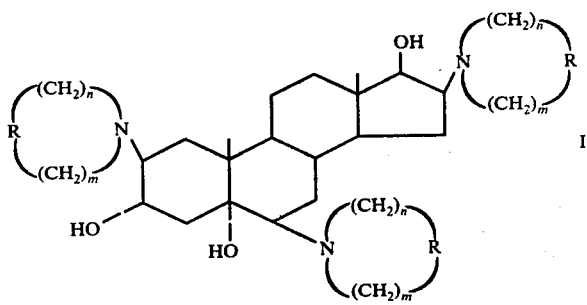

thus formed — wherein R, n and m are the same as above — with an aliphatic carboxylic acid having 1–5 carbon atoms or a reactive derivative thereof and converting the compound of the formula I thus formed, if desired, to an acid addition salt or to a quaternary salt of the compound of the formula Ia or Ib.

According to an embodiment of the process of the invention di- or triepoxy-androstane-derivatives preferably 2α,3α;16α,17α-diepoxy-5α-hydroxy-6β-chloro-17β-bromo-androstane or 2α,3α;16α,17α-diepoxy-5α,17β-diacetoxy-6β-chloro-androstane or 2α,3α;5α,6α;16α,17α-triepoxy-17β-bromo-androstane are reacted with a heterocyclic amine base of the formula V. The compounds of the formula V are heterocyclic amines consisting of 5 to 8 members, containing 1 or 2 nitrogen atoms, some advantageous representatives of which are e.g. N-alkyl-piperazine, N-alkyl-pirimidine, N-alkyl-imidazolidine, piperidine, pyrrolidine, and heptamethyleneimine. The alkyl chain in the N-alkylamines has 1 to 3 carbon atoms. As the reaction is accompanied by setting free an acid (hydrochloric acid and hydrogen bromide or acetic acid is set free) the amine of the formula V is used in an excess in order to bind the leaving acid.

The reaction is conducted at a temperature in the range of from room temperature to the boiling point of the reaction mixture, preferably at the boiling point of the reaction mixture in the presence of water, an inert solvent or acetonitrile or optionally without any solvent.

After the reaction is complete, the mixture is evaporated, the residue is dissolved in an organic solvent, preferably in chlorinated hydrocarbons or ether and washed with water or saturated sodium chloride solution until the pH value of 7 – 8 is achieved. After the separation of the layers the organic phase is evaporated and thus the compound of the formula IV is obtained.

If the product is prepared from diepoxy-5α,17α-diacetoxy-6β-chloro-androstane, the residue obtained after the evaporation of the reaction mixture is heated with an alcoholic alkali metal hydroxide solution. The formation of the epoxy ring from 5α-acetoxy and 6β-chloro-substituents is accomplished by the heating.

The alcoholic solution is evaporated and the product of the formula IV is obtained from the residue by the method described above.

The compound of the formula V prepared as described above is reduced. As a reducing agent alkali metal borohydride, preferably sodium borohydride or an alkoxy metal hydride, preferably sodium-bis(2-methoxyethoxy)-lithium-aluminumhydride or dimethoxy-borohydride can be used.

The reduction is conducted in a solvent, preferably in a lower alkyl alcohol, in a chlorinated hydrocarbon or tetrahydrofuran, preferably in a solvent mixture of two components. The reducing agent is added to the reaction mixture alone or in the form of an aqueous suspension. The reaction is conducted at a temperature below 0° C. The reaction product (compound of the formula III) is isolated by evaporation and purified if desired, by stirring with water and ether. The crude product of the formula III is optionally heated with an alcoholic alkali metal hydroxide solution before the purification.

The obtained compound of the formula III is repeatedly reacted with the amine of the formula V. The mono-aminoandrostane of the formula III is converted directly to the suitable triaminoandrostane derivative. As a compound of the formula V such compound is used wherein R is of the same meaning as when preparing mono-aminoandrostane.

The amine of the formula V is used in great excess, i.e. in about 40 to 80-fold molar excess comparing with the compound of the formula III.

The reaction is preferably conducted in a bomb tube in the presence of water, at a temperature of 70° C to 160° C, particularly at 130° C to 150° C at a low pressure preferably at the tension of the mixture itself corresponding to the temperature. The compound of the formula II formed in the reaction is recovered e.g. by evaporation and is purified by mixing the compound with ether and acetonitrile.

The compound of the formula II, prepared as described above is converted to a compound of the formula I by acylation. Among the 3 hydroxyl groups of the compound of the formula II only 2 are acylated under the reaction conditions. The hydroxyl group at the 5 position remains unchanged due to steric hindrance.

As an acylating agent an aliphatic carboxylic acid having 1 to 5 carbon atoms or reactive derivative corresponding to the acid such as acid halogenide, or preferably a suitable acid anhydride, such as acetic acid anhydride or propionic acid anhydride are used.

The acylation is conducted preferably in the presence of a Lewis acid such as iron(III)chloride, antimony chloride, tin chloride or preferably zinc chloride. Instead of a Lewis acid a tertiary amine or sodium acetate may be used and the acylation can be carried out without any catalyst as well.

After the acylation is completed the acylating agent used in excess is decomposed with water, and the pH-value is then adjusted to 8 to 10 and the precipitated compound of the formula I is isolated by filtration and by extraction and, if desired, purified.

The compounds of the formula I can be converted to non-toxic, pharmaceutically acceptable acid addition salts by a method known per se. The most advantageous inorganic acid addition salts are hydrogen halide acid addition salts, and among the organic acid addition salts, acetates and gluconates are preferred.

Compounds of the formula I are converted to di- or tri-quaternary salts of the formulae Ia or Ib. As quaternizing agents alkylhalogenides having 1 to 5 carbon atoms such as methyl, ethyl, propyl, i-butyl-halogenide, preferably the appropriate bromo compound or allyl bromide are used.

If the triamino compound of the formula I contains 1—1 nitrogen, due to steric hindrance only a di-quaternary salt is formed even if the quaternizing agent is used in a great (about 20-25-fold) molar excess.

From heterocyclic triamines containing 2—2 nitrogens in all the three hetero rings the sterically less inhibited nitrogen — being further from the steroid nucleus — can be quaternized i.e. a triquaternary salt is obtained.

The molar ratio of the compound of the formula I and the quaternizing agent is changed according to the length of the alkyl chain, methyl bromide is preferably used in a ratio of 1 : 6 propyl bromide in a ratio of 1 : 60 in order to obtain a triquaternary salt.

The compounds of the formula I and the acid addition salts thereof and the quaternary salts thereof of the formulae Ia and Ib of the invention can be converted to a pharmaceutical composition by using the pharmaceutically acceptable carriers and/or excipients, preferably compositions suitable for parenteral administration are prepared.

As carriers non-toxic, inert substances, preferably water, or sterile physiological sodium chloride solution is used.

As excipients preservatives, stabilizers or buffers are preferred.

The process according to the invention is further illustrated by the following Examples:

EXAMPLE 1

2α,3α,5α,6α-Diepoxy-17-oxo-16β-piperidinoandrostane a. 13.5 g (0.032 mole) of 2α,3α;16α,17α-diepoxy-5α-hydroxy-6β-chloro-17β-bromo-androstane are dissolved in 100 ml. of acetonitrile and 11 ml. (0.111 mole) of piperidine are added. The reaction mixture is heated for 1 hour under reflux and is evaporated at reduced pressure. The residue is dissolved in chloroform, washed with a solution of sodium chloride and water until a pH value of 7 to 7.5 is achieved. The two layers are separated. The chloroform layer is dried over sodium sulfate, filtered and the filtrate is evaporated to dryness. The crystalline residue is purified by admixing it with ether, the mixture is filtered and dried. Yield: 10.3 g (82.6%) of 2α,3α;5α,6α-diepoxy-17-oxo-16β-piperidino-androstane. M.p.: 187°–190° C.

$[\alpha]_D^{25} = +31.7°$ ($c = 1$, in chloroform)

Analysis: for the formula $C_{24}H_{35}NO_3$; Calculated: C 74.80%; H 9.11%; N 3.64%; found: C 74.59%; H 8.97%; N 3.47%.

b. 6.0 g. (0.157 mole) of 2α,3α; 5α,6α;16α,17α-triepoxy-17β-bromo-androstane are dissolved in 45 ml. of acetonitrile and 6.4 ml. (0.0647 mole) of piperidine are added. The reaction mixture is heated under reflux for 1 hour and evaporated at reduced pressure. The residue is dissolved in ether whereafter the ethereal solution is washed first with a saturated sodium chloride solution then with water. The 2 layers are separated, the water is removed from the ether layer with sodium sulfate, the residue is filtered. The residue is triturated with ether cooled to 0° C, the precipitated product is filtered, dried. The physical constants and the product are identical with those given in Example 1a.

c. 26.2 g (0.06 mole) of 2α,3α,16α,17α-diepoxy-5α,17β-diacetoxy-6β-chloro-androstane are dissolved in the mixture of 221 ml. (2.6 moles) of piperidine and 35 ml. of water. The reaction mixture is allowed to stand at a temperature of 94°–96° C for 2 hours, whereafter it is evaporated at reduced pressure at a temperature of below 50° C. The residue is dissolved in 200 ml. of methanol containing 2 g. of sodium hydroxide and the solution is heated under reflux for 20 minutes and evaporated at reduced pressure. The residue is dissolved in 600 ml. of ether and the ether solution is washed with a saturated sodium chloride solution until a pH of 7 – 8. The two layers are separated and the ether layer is worked up as described in Example 1b.

The product and the physical constants of the product are the same as given in Example 1a. Preparation of the starting materials:

The starting material of Example 1a: 2α,3α,16α,17α-diepoxy-5α-hydroxy-6β-chloro-17β-bromo-androstane 50 g. (0.164 mole) of 5α,6β-dihydroxy-17-oxo-androst-2-ene are dissolved in the mixture of 550 ml. of ethanol and 93 ml. of triethylamine and 163 ml. of 98% of hydrazine hydrate (3.28 moles) are added. The reaction mixture is heated under reflux for 2 hours whereafter the ethanol is distilled off. The residue is triturated with 300 ml. of ether cooled to 0° C. the precipitated product is filtered and washed with ether and water to remove triethylamine. The obtained product is dried at reduced pressure over phosphorus pentoxide and recrystallized, if desired from methanol.

Yield: 50 g. (95%) of 5α,6β-dihydroxy-androst-2-ene-17-hydrazone

M.p.: 230° – 232° C $[\alpha]_D^{25} = +44.1°$ (c = 1, in chloroform).

Analysis for the formula: $C_{19}H_{30}N_2O_2$; calculated: C 72.0%; H 9.43%; N 8.80%; found: C 71.8%; H 9.18%; N 9.00%.

290 g. (0.91 mole) of 5α,6β-dihydroxy-androst-2-ene-17-hydrazone are dissolved in 4350 ml. of anhydrous pyridine and the solution is cooled to −10° C. 186 g. (1.23 mole) of N-bromo-succinic imide are added in 1950 ml. of pyridine at a temperature of 0°–10° C to the solution. The reaction mixture is stirred until the nitrogen evolution is stopped, whereafter the mixture is added to 32 l. of 10% icy hydrochloric acid solution.

The precipitated substance is filtered, washed with water until neutral and dried at a temperature of not lower than 40° C. The precipitated substance is filtered, washed with water until neutral and dried at a temperature of not higher than 40° C. The product is mixed with a 40-fold amount of ether.

The insoluble side product is filtered, the ether filtrate is evaporated and the obtained oily residue is purified with 250 ml. of n-hexane. The precipitated crystalline product is filtered and dried.

Yield: 130 g. (38%) of 5α,6β-dihydroxy-17-bromo-androsta-2,16-diene.

M.p.: 170° – 175° C.

$[\alpha]_D^{25} = +25.1°$ (c = 1, in chloroform)

Analysis: for the formula $C_{19}H_{27}BrO_2$; calculated: C 62.20%; H 7.35%; Br 21.8%; found: C 62.0%; H 7.12%; Br 21.6%.

95 g. (0.258 mole) of 5α,6β-dihydroxy-17-bromo-androsta-2,16-diene are dissolved in 950 ml. of anhydrous pyridine whereafter 21 ml. (0.276 mole) of methanesulfonic acid chloride are added under stirring at room temperature. The reaction mixture is allowed to stand for 16 hours and it is added to 9 l. of icy water under vigorous stirring and the precipitated substance which is difficult to work is extracted with 1500 ml. of methylene chloride. The methylene chloride extract is washed with 10% aqueous hydrochloric acid solution to remove pyridine followed by washing with water to adjust the pH of the solution to neutral, the mixture is then dried over sodium sulfate, and evaporated to dryness. The residue — i.e. a mixture of 5α-hydroxy-6β-chloro-17-bromo-androsta-2,16-diene and of 5α,6α-epoxy-17-bromo-androsta-2,16-diene is dissolved in diethylether and ether in hydrochloric acid is added until the value of pH of 2–3 is achieved and the 5α-hydroxy-6β-chloro-17-bromo-androsta-2,16-diene thus formed is purified with a 10-fold amount of petroleum ether at room temperature.

Yield: 79.0 g. (79.0%) of 5α-hydroxy-6β-chloro-17-bromo-androsta-2,16-diene.

M.p.: 125°–126° C. $[\alpha]_D^{25} = +3.8°$ (c = 1, in chloroform)

Analysis: for the formula $C_{19}H_{26}Br$ ClO; calculated: C 59.10%; H 6.73%; Br 20.62%; Cl 9.17%; found: C 53.9%; H 6.51%; Br 20.37%; Cl 8.7%.

42 g. (0.109 mole) of 5α-hydroxy-6β-hydroxy-6β-chloro-17-bromo-androsta-2,16-diene are dissolved in 360 ml. of chloroform and 915 ml. of 5% chloroform solution of perbenzoic acid (0.332 mole) are added. The reaction mixture is allowed to stand at room temperature for 16 hours, whereafter it is washed with 10% sodium hydroxide solution at 0° to 5° C and then with water until a pH value of 7 is achieved. The 2 aqueous layers are separated, the chloroform layer is dried over sodium sulfate, filtered and the filtrate is evaporated to dryness. The residue is recrystallized from acetonitrile.

Yield: 43 g. (94%) of 2α, 3α;16α,17α-diepoxy-5α-hydroxy-6β-chloro-17-bromo-androstane.

M.p.: 150°–152° C.

$[\alpha]_D^{25} = +19.5°$ (c = 1, in chloroform).

Analysis for the formula $C_{19}H_{26}BrClO_3$; calculated: C 54.60%; H 6.22%; Br 19.10%; Cl 8.50%; found: C 54.41%; H 6.00%; Br 18.79%; Cl 8.30%.

Preparation of the starting material of Example 1b: 2α,3α; 5α,6α16α;17α-triepoxy-17β-bromo-androstane The mixture of the compounds obtained in the course of the preparation of the starting material of Example 1a: (5α-hydroxy-6β-chloro-17-bromo-androsta-2,16-diene and 5α,6α-epoxy-17-bromo-androsta-2,16-diene) is dissolved in a 16 fold amount — calculated for the starting material — of 5α,6β-dihydroxy-17-bromo-androsta-2,16-diene, whereafter a 12% aqueous sodium hydroxide solution corresponding to one fifth of the starting material is added. The reaction mixture is heated for 10 minutes under reflux, cooled to room temperature and the pH value of the mixture is adjusted to 7 by acetic acid. The solvent is distilled, the residue is triturated with water the precipitated product is filtered, washed with water until neutral and the product is dried over phosphorus pentoxide in vacuo. The obtained product is crystallized from acetonitrile.

Yield: 89% of 5α, 6α-epoxy-17-bromo-androsta-2,16-diene

M.p.: 146°–147° C $[\alpha]_D^{25} = 18.3°$ (c = 1, in chloroform)

Analysis for the formula $C_{19}H_{25}BrO$; calculated: C 65.40%; H 7.16%; Br 22.80%; found: C 65.20%; H 6.98%; Br 22.57%.

19.5 g. (0.056 mole) of 5α,6α-epoxy-17-bromo-androsta-2,16-diene are dissolved in 125 ml. of chloroform, whereafter 460 ml. of 5% chloroform solution of perbenzoic acid (0.168 mole) are added. The reaction mixture is allowed to stand for 16 hours at room temperature cooled to 0° to 5° C and washed with 10% sodium hydroxide solution, then with water until the pH value of 7 is achieved. The chloroform layer is separated, dried on sodium sulfate, filtered and the filtrate is evaporated to dryness. The residue is triturated with a 10-fold amount of ether and the precipitated crystalline product is recrystallized, if desired, from acetonitrile.

Yield: 20 g. (94%) of 2α,3α;5α,6α;16α,17α-triepoxy-17-bromo-androstane.

M.p.: 206°–209° C $[\alpha]_D^{25} = +33.3°$ (c = 1, in chloroform)

Analysis for the formula $C_{19}H_{25}BrO_3$; calculated: C 59.80%; H 6.60%; Br 20.94%; found: C 59.68%; H 6.91%; Br 20.7%.

The preparation of the starting material of the Example 1c:

2α,3α,16α,17α-diepoxy-5α,17β-diacetoxy-6β-chloro-androstane.

50 g. (0.16 mole) of 5α,6β-dihydroxy-17-oxo-androst-2-ene are dissolved in 500 ml. of anhydrous pyridine and 30 g. (0.26 mole) of methanesulfonic acid chloride are added. The reaction mixture is allowed to stand for 16 hours at room temperature and is then added to 5 l. of icy water. The precipitated crude product is filtered, and washed with 10% aqueous hydrochloric acid solution to remove pyridine and then with water to achieve a pH of 7 and the product is dried over phosphorus pentoxide in vacuo. The product thus obtained is dissolved in a 20-fold amount of acetone and the mixture is clarified with silicagel under stirring. The mixture is slowly filtered and the filtrate is concentrated to form a syrup-like substance and the precipitated product is filtered and dried.

Yield: 47 g (88%) of 5α-hydroxy-6β-chloro-17-oxo-androst-2-ene.

M.p.: 178°–180° C.

$[\alpha]_D^{25} = +59.8°$ ($c = 1$, in chloroform)

Analysis for the formula $C_{19}H_{27}ClO_2$; calculated: C 70.6%; H 8.6%; Cl 11.0%; found: C 70.4%; H 8.63%; Cl 10.8%.

30 g. (0.09 mole) of 5α-hydroxy-6β-chloro-17-oxo-androsta-2-ene are dissolved in 60 ml. of just distilled isopropyenyl-acetate and 1.5 g. of p-toluene-sulfonic acid are added. The reaction mixture is steadily heated for 1.5 hours by using a 80 cm. long mirror column packed with Raschig-rings to achieve the boiling point of the reaction mixture and the acetone formed in the reaction is continuously distilled. After distilling for about 8 hours the reaction mixture is cooled to room temperature and added to 3500 ml. of icy water. The precipitated oily product is extracted with 2×300 ml. of ether, the combined ether extracts are cooled to 0°–5° C and under inner cooling the ether solution is washed with 5% aqueous sodium hydroxide solution to remove the acid. The ether layer is separated, dried over sodium sulfate, filtered and the ether and the unreacted isopropenyl acetate are distilled from the filtrate. The residue of oily consistence is subjected to column chromatography on a column packed with 180 g. of silicagel of a particle size of 0.003 to 0.200 mm. and eluted with hexane containing 5% ether.

The eluate fractions are identified with thin layer chromatography (adsorbent: silicagel, developing solvent: a mixture of benzene and acetone 8:2) the eluate fractions are combined and evaporated. The residue is recrystallized from methanol.

Yield: 25 g. (74%) of 5α,17β-diacetoxy-6β-chloro-androsta-2,16-diene.

M.p.: 127°–129° C.

$[\alpha]_D^{25} = -14.8°$ ($c = 1$, in chloroform)

Analysis for the formula $C_{23}H_{31}ClO_4$; calculated: C 67.8%; H 7.6%; Cl 3.7%; found: C 67.7%; H 7.3%; Cl 8.5%.

20.5 g (0.054 mole) of 5α,17β-diacetoxy-6β-chloro-androsta-2,16-diene are dissolved in 100 ml. of benzene and 400 ml. of 7% perbenzoic acid in ether are added. The reaction mixture is then allowed to stand at room temperature, cooled to 0° to 5° C and washed with an aqueous sodium hydroxide solution and with water until the pH value achieves 7. The layers are dried over sodium sulfate and the solvent is removed by distillation. The residue is triturated with 100 ml. of ether, filtered and dried.

Yield: 16.8 g. (76%) of 2α, 3α;16α,17α-diepoxy-5α17β-diacetoxy-6-chloro-androstane M.p.: 164° – 168° C $[\alpha]_D^{25} = -1.1°$ ($c = 1$, in chloroform)

Analysis for the formula $C_{23}H_{31}ClO_6$; calculated: C 62.9%; H 7.0%; Cl 8.0%; found: C 62.68%; H 7.11%; Cl 7.9%.

EXAMPLE 2

2α,3α;15α,6α-Diepoxy-17-oxo-16β-N-methyl-piperazino-androstane

The compound is prepared from 2α,3α,16α,17α-diepoxy-5α-hydroxy-6β-chloro-17-bromo-androstane and N-methylpiperazine by a method described in Example 1a, with a yield of 81%, or from 2α,3α;5α,6α;-16α,17α-triepoxy-17-bromo-androstane and N-methylpiperazine according to the method described in Example 1b, with a yield of 76%, or from 2α,3α;16α,17α-diepoxy-5α,17β-diacetoxy-6β-chloro-androstane and N-methyl-piperazine with a yield of 75%.

M.p.: 149°–151° C.

$[\alpha]_D^{25} = +32.8°$ ($c = 1$, in chloroform)

Analysis for the formula $C_{24}H_{36}N_2O_2$; calculated: C 72.00%; H 9.00%; N 7.00%; found: C 71.78%; H 8.92%; N 6.79%.

EXAMPLE 3

2α,3α,5α,6α-Diepoxy-17β-hydroxy-16β-piperidino-androstane 8 g. (0.0208 mole) of 2α,3α,5α,6α-diepoxy-17-oxo-16β-piperidino-androstane are dissolved in 36 ml. of tetrahydrofuran and 15 ml. of methanol and a suspension of 5 g. (0.132 moles) of sodium borohydride in 9 ml. of water are added. The reaction mixture is stirred for 8 hours, and evaporated to dryness at a temperature of below 40° C. The residue is triturated with water and the precipitated crude product is filtered, the precipitation is purified with ether, filtered and dried.

Yield: 6.4 g. (79.5%) of 2α,3α,5α,6α-diepoxy-17β-hydroxy-16β-piperidino-androstane.

M.p.: 184°–188° C.

$[\alpha]_D^{25} = -42.7°$ ($c = 1$, in chloroform)

Analysis for the formula $C_{24}H_{37}NO_3$; calculated: C 74.40%; H 9.55%; N 3.62%; found: C 74.18%; H 9.50%; N 3.47%.

EXAMPLE 4

2α,3α;5α,6α-Diepoxy-17β-hydroxy-16β-N-methyl-piperazine-androstane

The compound is prepared from 11.4 g. (0.285 mole) of 2α,3α;5α,6α-diepoxy-17-oxo-16β-N-methyl-piperazino-androstane by reduction with sodium borohydride according to Example 3. The purification of the crude product is carried out as follows: the precipitated substance is dissolved in methanol and the solution is heated with 0.5 g. of sodium hydroxide under reflux for half an hour and the solvent is distilled. The residue is washed with saturated sodium chloride solution and with water, the solution is filtered and dried over phosphorus pentoxide.

Yield: 10.2 g. (88%) of 2α,3α,5α,6α-diepoxy-17β-hydroxy-16β-N-methyl-piperazino-androstane.

M.p.: 177°–179° C.

$[\alpha]_D^{25} = -47.5°$ ($c = 1$, in chloroform)

Analysis for the formula $C_{24}H_{38}N_2O_3$; calculated: C 71.70%; H 9.46%; N 6.98%; found: C 71.70%; H 9.23%; N 6.71%.

EXAMPLE 5

2β,6β,16β-Tripiperidino-3α,5α,17β-trihydroxy-androstane 6 g. (0.0155 mole) of 2α,3α;5α,6α-diepoxy-17β-hydroxy-16β-piperidino-androstane are dissolved in a mixture of 60 ml. (0.606 mole) of piperidine and 10 ml. of water. The reaction mixture is heated in a bomb tube for 72 hours at an outer temperature of 140° C. After the reaction is complete, the reaction mixture is evaporated to dryness, the residue is triturated with ether and the precipitated crystalline product is filtered and heated in acetonitrile under reflux. The purified product is filtered and dried.

Yield: 6.7 g. (78.5%) of 2β, 6β,16β-tripiperidino-3α,-5α,17β-trihydroxy-androstane M.p.: 6.7 g. (78.5%)

$[\alpha]_D^{25} = +19.3°$ (c = 1, in chloroform)

Analysis for the formula $C_{34}H_{55}N_3O_3$; calculated: C 73.70%; H 9.55%; N 7.60%; found: C 73.58%; H 9.75%; N 7.42%.

EXAMPLE 6

2β,6β,16β-Tri-N-methyl-piperazino-3α,5α,17β-trihydroxy-androstane

The compound is prepared from 2α,3α;5α,6α-diepoxy-17β-hydroxy-16β-N-methyl-piperazino-androstane according to Example 5.

Yield: 6 g. (80.0%)

M.p.: 207°–210° C $[\alpha]_D^{25} = 10.6°$ (c = 1, in chloroform)

Analysis for the formula $C_{34}H_{61}N_6O_3$; calculated: C 68.00%; H 10.12%; N 13.94%; found: C 67.71%; H 9.92%; N 13.68%.

EXAMPLE 7

2β, 6β,16β-Tri-N-methyl-piperazino-3α,17β-diacetoxy-5α-hydroxy-androstane 2 g. (0.0029 mole) of 2β,6β,16β-tri-N-methyl-piperazino-3α,5α,17β-trihydroxy-androstane are dissolved in the mixture of 9 ml. of acetic acid anhydride and 0.6 ml. of glacial acetic acid and 0.3 g. of zinc chloride are added. The reaction mixture is stirred at room temperature for 12 hours and 30 ml. of water are added to the mixture and it is stirred for another 2 hours. The aqueous solution is cooled to 0° to 5° C and the pH is adjusted at the same temperature to 8 – 10 by adding a 10% aqueous sodium hydroxide solution. The precipitated fluffy substance is immediately extracted with ether. The ether extract is washed with saturated sodium chloride and/or water to achieve pH = 7. The layers are separated. The ether phase is dried over sodium sulfate, filtered and evaporated to dryness. The residue is dissolved in ether, clarified with silicagel and the silicagel is removed from the mixture by filtration. The filtrate is evaporated to dryness and the residue is, if desired, triturated with n-hexane, filtered and dried.

Yield: 1.7 g. (75.5%) of 2β,6β,16β-tri-N-methyl-piperazino-3α,17β-diacetoxy-5α-hydroxy-androstane.

M.p.: 150°–153° C.

$[\alpha]_D^{25} = -3.3°$ (c = 1, in chloroform)

Analysis for the formula $C_{38}H_{66}N_6O_5$; calculated: C 66.40%; H 9.62%; N 12.22%; found: C 66.25%; H 9.31%; N 12.05%.

EXAMPLE 8

2β,6β,16β-Tripiperidino-3α,17β-diacetoxy-5α-hydroxy-androstane

The compound is prepared from 2β,6β,16β-tripiperidino-3α,17β-trihydroxy-androstane according to Example 7.

Yield: 77.0% of 2β,6β,16β-tripiperidino-3α,17β-diacetoxy-5α-hydroxy-androstane

M.p.: 104°–105° C (decomposition)

$[\alpha]_D^{25} = -7.3°$ (c = 1, in chloroform).

Analysis for the formula $C_{38}H_{59}N_3O_5$; calculated: C 71.60%; H 9.27%; N 6.60%; found: C 71.50%; H 9.00%; N 6.38%.

EXAMPLE 9

2β,6β,16β-Tri-(4-dimethyl-piperazino)-3α,17β-diacetoxy-5α-hydroxy-androstane-tribromide 0.5 g. (0.73 mmole) of 2β,6β,16β-tri-N-methyl-piperazino-3α,17β-diacetoxy-5α-hydroxy-androstane are dissolved in 50 ml. of acetone whereafter 5 ml. of a 8% solution of methylbromide (4.2 mmole) in acetone are added. The reaction mixture is allowed to stand for 16 hours and the precipitated product is filtered, washed with ether and the filtered product is heated in acetone under reflux. The crystalline solution is filtered and dried.

Yield: 0.67 g. (95.5%) of 2β,6β,16β-tri-(4-methyl-piperazino)-3α,17β-diacetoxy-5α-hydroxy-androstane-tribromide M.p.: 247°–250° C (decomposition)

$[\alpha]_D^{25} = 0°$ (c = 1, in chloroform)

Analysis for the formula $C_{41}H_{75}Br_3N_6O_5$; calculated: C 50.70%; H 7.71%; Br 24.72%; N 8.66%; found: C 50.62%; H 7.58%; Br 24.41%; N 8.76%.

EXAMPLE 10

2β,6β,16β-Tri-(4-propyl-4-methyl-piperazino)-3α,17β-diacetoxy-5α-hydroxy-androstane-tribromide 0.5 g. (0.00073 mole) of 2β,6β,16β-tri-N-methyl-piperazino-3α,17β-diacetoxy-5α-hydroxy-androstane are dissolved in 10 ml. of acetonitrile whereafter 4 ml. (0.0442 mole) of propyl bromide are added. The reaction mixture is heated for 2 hours under reflux followed by cooling to room temperature and by dilution with ether to a 5-fold volume. The precipitated quaternary salt is filtered, washed with ether and dried at reduced pressure.

Yield: 0.65 g (84.5%) of 2β,6β,16β-tri-(4-propyl-4-methyl-piperazino)- 3α,17β-diacetoxy-5α-hydroxy-androstane-tri-bromide M.p.: 245°–248° C (decomposition)

Analysis for the formula $C_{47}H_{87}N_6O_5Br_3$; calculated: C 52.50%; H 8.25%; N 7.96%; Br 22.70%; found: C 52.41%; H 8.1%; N 7.70%; Br 22.45%.

EXAMPLE 11

2β,11β-bis-N-Methyl-piperidino-3α,17β-diacetoxy-5α-hydroxy-androstane-dibromide 0.5 g. (0.785 mmole) of 2β,6β,16β-tri-piperidino-3α,17β-diacetoxy-5α-hydroxy-androstane are dissolved in 20 ml. of acetone whereafter 20 ml. of a 8% solution of methyl bromide (16.9 mmole) in acetone are added. The reaction mixture is allowed to stand for 1 week at room temperature followed by precipitating the product by dilution with ether. The precipitated diquaternary product is filtered, washed with acetone at a temperature of 5°–10° C. and dried.

Yield: 0.6 g. (92%) of 2β,16β-bis-N-methyl-piperidino-6β-piperidino-3α,17β-diacetoxy-5α-hydroxy-androstane-dibromide.

M.p.: 187° C (decomposition)

$[\alpha]_D^{25} = +2.9°$ (c = 1, in chloroform).

Analysis: for the formula $C_{40}H_{65}Br_2N_3O_5$; calculated: C 58.00%; H 7.85%; Br 19.22%; N 5.06%; found: C 57.78%; H 7.90%; Br 18.92%; N 5.10%.

EXAMPLE 12

2β,6β,16β-Tri-(4-dimethyl-piperazino)-3α,17β-diacetoxy-5α-hydroxy-androstane-tribromide injection 1 mg. of 2β,6β,16β-tri-(4-dimethyl-piperazino)-3α,17β -diacetoxy-5α-hydroxy-androstane-tribromide are dissolved in sterile physiological sodium chloride solution and the solution is filled into brown injection vials of a volume of 2 ml. followed by sterilization of the solution.

What we claim is:

1. A process for the preparation of new triaminoandrostanes or the acid additional salts thereof of the formula

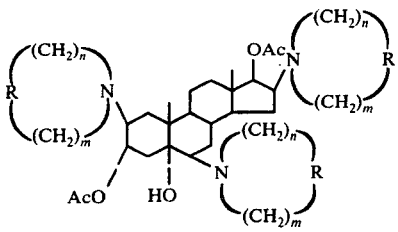

wherein
Ac is an alkylcarbonyl group having 1 to 4 carbon atoms in the alkyl moiety
R is methylene or N-R$_2$ wherein R$_2$ is C$_{1-3}$ alkyl and all three substituents R of the same meaning,
n is 2
m is 2 and for the preparation of di-quaternary salts thereof of the formula

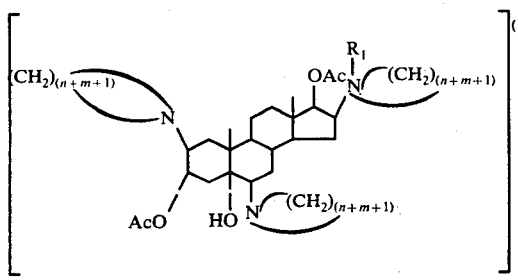

and for the preparation of tri-quaternary salts thereof of the formula

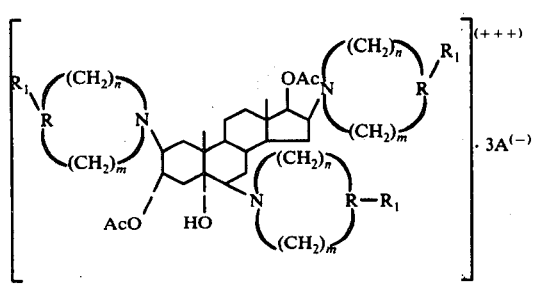

wherein
Ac, R, n and m are defined above,
R$_1$ is alkyl having 1 to 5 carbon atoms and
A is a halogen atom, which comprises reacting an epoxy-androstane with a compound of the formula

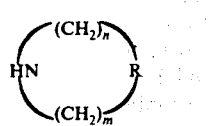

wherein R, n, and m are as defined above and reducing the compound of the formula

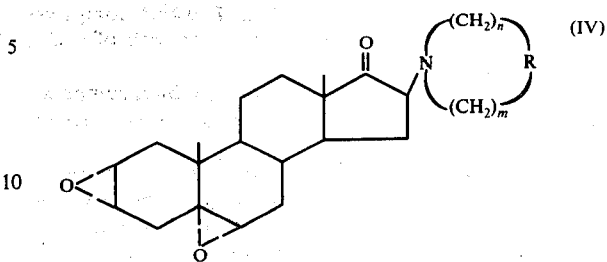

thus formed, and reacting a compound of the formula

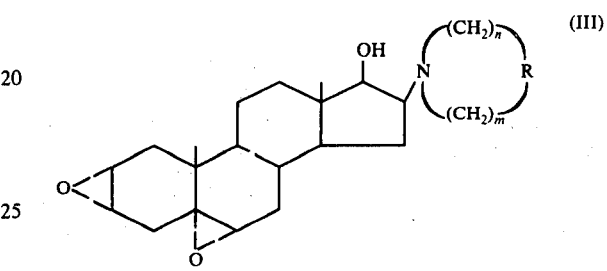

thus obtained again with a compound of the formula V — wherein R, n and m are defined above — with the restriction that R in the latter compound of the formula V is the same as in the first step — and acylating the compound of the formula

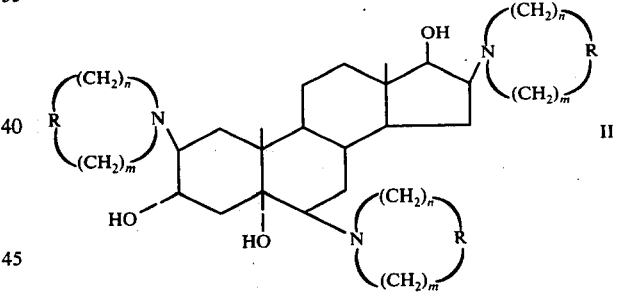

wherein the substituents are as defined above — with a C$_{1-5}$ aliphatic carboxylic acid, carboxylic acid halogenide or carboxylic acid anhydride and converting the obtained compound of the formula I, if desired, into acid addition salts or quaternary salts of the formulae Ia or Ib.

2. A process according to claim 1, which comprises conducting the reaction of the starting di- or triepoxyandrostane and of the compound of the formula V in the presence of a base preferably in an excess of the compound of the formula V.

3. A process as claimed in claim 1, which comprises reacting a compound of the formula IV with a metal hydride.

4. A process according to claim 1, which comprises carrying out the reduction at a temperature of below 40° C.

5. A process as claimed in claim 1, which comprises reacting the compounds of the formulae III and V in a molar ratio of 1: (20–100).

6. A process according to claim 1, which comprises reacting the compounds of the formulae III and V at a temperature of 70° – 160° C.

7. A process as claimed in claim 1, which comprises reacting a compound of the formula II with of a $C_{1-5}$ aliphatic carboxylic acid anhydride.

8. A process as claimed in claim 7, which comprises conducting the acylation in the presence of a Lewis acid.

9. Process according to claim 1, which comprises carrying out the reactions in the presence of a solvent.

10. A process according to the claim 1, which comprises using a quaternizing agent in an excess of 10 to 50-fold molar excess for the preparation of the di-quaternary salt of the formula I$a$.

11. A process as claimed in claim 1, which comprises using the quaternizing agent in a molar excess of 3 – 80, for the preparation of the triquaternary salts of the formula I$b$.

12. A process according to claim 1, which comprises preparing 2$\beta$,6$\beta$,16$\beta$-tri-N-methyl-piperazino-3$\alpha$,17$\beta$-diacetoxy-5$\alpha$-hydroxy-androstane or an acid addition salt thereof.

13. A process according to claim 1, which comprises preparing 2$\beta$,6$\beta$,16$\beta$-tri-piperidino-3$\alpha$,17$\beta$-diacetoxy-5$\alpha$-hydroxy-androstane or an acid addition salt thereof.

14. A process according to claim 1, which comprises preparing 2$\beta$,6$\beta$,16$\beta$-tri-(4-dimethyl-piperazino)-3$\alpha$,17$\beta$-diacetoxy-5$\alpha$-hydroxy-androstane-tribromide.

15. A process according to claim 1, which comprises preparing 2$\beta$,6$\beta$,16$\beta$-tri-(4-propyl-4-methyl-piperazino)-3$\alpha$,17$\beta$-diacetoxy-5$\alpha$-hydroxy-androstane-tribromide.

16. A process according to claim 1, which comprises preparing 2$\beta$,16$\beta$-bis-N-methyl-piperidino-6$\beta$-piperidino-5$\alpha$-hydroxy-androstane-dibromide.

17. A compound of the formula

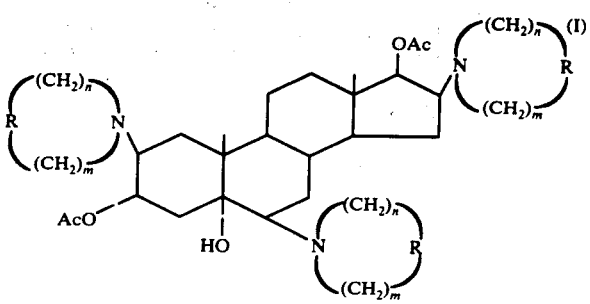

wherein
Ac is an alkylcarbonyl group containing 1 to 4 carbon atoms in the alkyl chain
R is methylene or

group — where $R_2$ is a $C_{1-3}$ alkyl, and all the three substituents R are of the same meaning
$n$ is 2
$m$ is 2 or a di-quaternary salt thereof of the formula

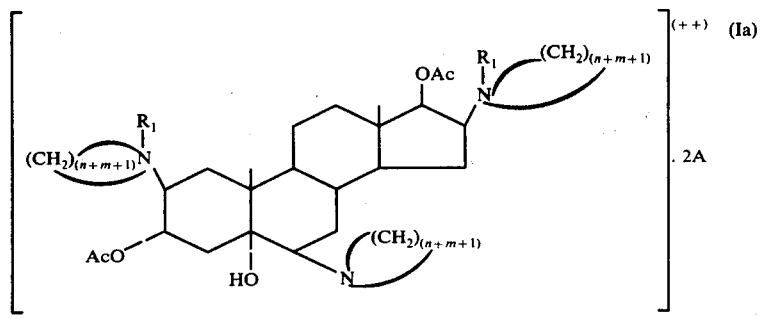

or a tri-quaternary salts thereof of the formula

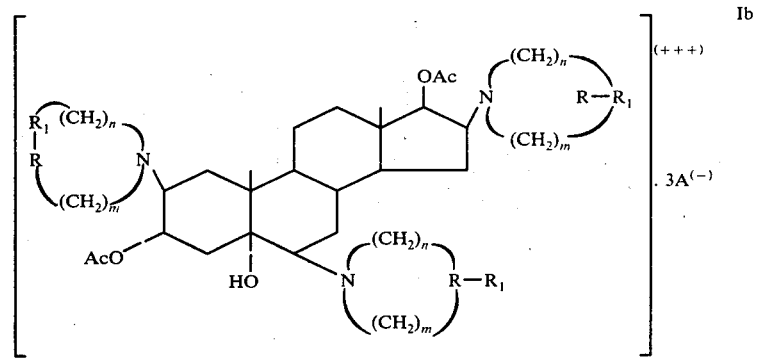

wherein
Ac, R, $n$ and $m$ are given above
$R_1$ is $C_{1-5}$ alkyl, and
A is halogen.

18. The compound defined in claim 17 which consists of 2$\beta$,6$\beta$,16$\beta$-Tri-N-methyl-piperazino-3$\alpha$,17$\beta$-diacetoxy-5$\alpha$-hydroxy-androstane.

19. The compound defined in claim 17 which consists of 2$\beta$,6$\beta$,16$\beta$-Tri-piperidino-3$\alpha$,17$\beta$-diacetoxy-5$\alpha$-hydroxy-androstane.

20. The compound defined in claim 17 which consists of 2β,6β,16β-Tri-(4-dimethyl-piperazino)-3α,17β-diacetoxy-5α-hydroxy-androstane-tribromide.

21. The compound defined in claim 17 which consists of 2β,6β,16β-Tri-(4-propyl-4-methyl-piperazino)-3α,17β-diacetoxy-5α-hydroxy-androstane-tribromide.

22. The compound defined in claim 17 which consists of 2β,16β-bis-N-methyl-piperidino-6β-piperidino-5α-hydroxy-androstane-dibromide.

* * * * *

UNITED STATES PATENT AND TRADEMARK OFFICE
CERTIFICATE OF CORRECTION

PATENT NO. : 4 071 515
DATED : 31 January 1978
INVENTOR(S) : Zoltan Tuba et al

It is certified that error appears in the above-identified patent and that said Letters Patent are hereby corrected as shown below:

The formula Ib in column 16 should read:

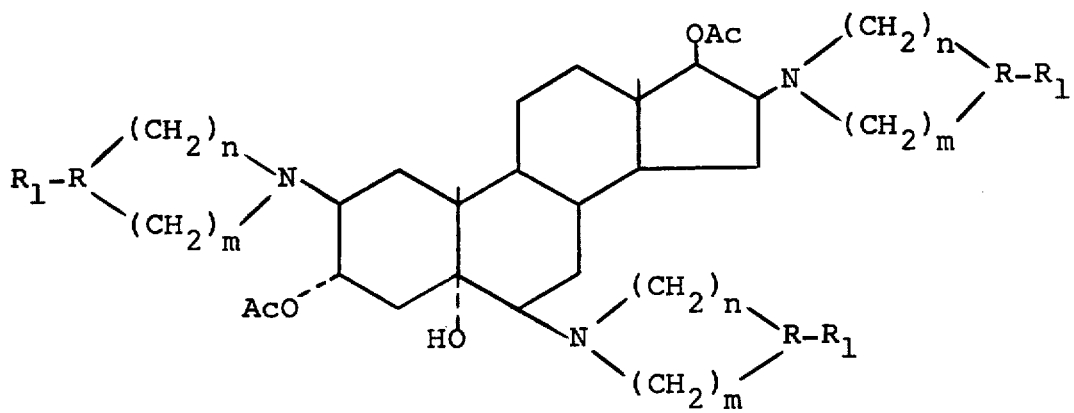

Signed and Sealed this

Twenty-second Day of May 1979

[SEAL]

Attest:

RUTH C. MASON
Attesting Officer

DONALD W. BANNER
Commissioner of Patents and Trademark